United States Patent
Adamczyk et al.

(10) Patent No.: US 10,568,749 B2
(45) Date of Patent: Feb. 25, 2020

(54) PROSTHETIC MANIPULATOR AND METHOD THEREFOR

(71) Applicant: Wisconsin Alumni Research Foundation, Madison, WI (US)

(72) Inventors: Peter Gabriel Adamczyk, Madison, WI (US); Ivan F. Ekman Simões, Rio de Janeiro (BR)

(73) Assignee: Wisconsin Alumni Research Foundation, Madison, WI (US)

( * ) Notice: Subject to any disclaimer, the term of this patent is extended or adjusted under 35 U.S.C. 154(b) by 18 days.

(21) Appl. No.: 15/171,519

(22) Filed: Jun. 2, 2016

(65) Prior Publication Data

US 2017/0348118 A1 Dec. 7, 2017

(51) Int. Cl.
A61F 2/66 (2006.01)
A61F 2/76 (2006.01)
A61F 2/70 (2006.01)
A61F 2/68 (2006.01)

(52) U.S. Cl.
CPC .............. *A61F 2/66* (2013.01); *A61F 2/6607* (2013.01); *A61F 2/68* (2013.01); *A61F 2002/6614* (2013.01); *A61F 2002/6854* (2013.01); *A61F 2002/701* (2013.01); *A61F 2002/704* (2013.01); *A61F 2002/764* (2013.01); *A61F 2002/7635* (2013.01)

(58) Field of Classification Search
CPC .. A61F 2/66; A61F 2/6607; A61F 2002/6854; B25J 9/0006
See application file for complete search history.

(56) References Cited

U.S. PATENT DOCUMENTS

| | | | | |
|---|---|---|---|---|
| 8,740,991 B2* | 6/2014 | Moser | ................... | A61F 2/6607 623/47 |
| 2003/0163206 A1* | 8/2003 | Yasui | ........................ | A61F 2/60 623/24 |
| 2007/0156252 A1* | 7/2007 | Jonsson | ..................... | A61F 2/66 623/24 |
| 2012/0232672 A1* | 9/2012 | Ragnarsdottir | ........... | A61F 2/68 623/24 |

(Continued)

OTHER PUBLICATIONS

Endolite (Sep. 2015). "élan: Open up your world [Brochure]". Miamisburg, Ohio.

(Continued)

*Primary Examiner* — Christie L Bahena
(74) *Attorney, Agent, or Firm* — Crawford Maunu PLLC

(57) ABSTRACT

Various aspects of the present disclosure characterize apparatuses and/or methods as may be implemented with a variety of prosthetic components and applications. As may be consistent with one or more embodiments described herein, respective manipulators are operable and/or operate to manipulate a prosthetic foot component about respective (e.g., separate) axes. A sensor circuit senses movement characteristics of the prosthetic foot component (e.g., movement, surroundings, and/or load applied due to movement). The manipulators operate with the sensor circuit to manipulate the prosthetic foot component about the axes in response to the sensed movement characteristics indicating that the prosthetic foot component is elevated over a surface.

24 Claims, 5 Drawing Sheets

(56) References Cited

U.S. PATENT DOCUMENTS

| | | | |
|---|---|---|---|
| 2014/0074243 A1* | 3/2014 | Holgate | A61F 2/30 623/18.11 |
| 2015/0066153 A1* | 3/2015 | Palmer, III | A61F 2/6607 623/24 |
| 2015/0265425 A1* | 9/2015 | Aagaah | A61F 2/6607 623/47 |
| 2016/0058581 A1* | 3/2016 | Maitland | A61F 2/66 623/53 |

OTHER PUBLICATIONS

Mitchell (Oct. 25, 2013). "The BiOM® T2 System [Brochure]". University of Rhode Island: BME 281 Presentation.

Orthocare Innovations, LLC. "megellan™ [Webpage]". Mountlake Terrace, WA (downloaded from the internet on Jul. 14, 2016 http://orthocareinnovations.com/magellan/).

Össur Dynamic Solutions. "Proprio Foot® [Catalogue page]". (downloaded from the internet on Jul. 14, 2016 http://www.ossur.com/prosthetic-solutions/products/dynamic-solutions/proprio-foot).

\* cited by examiner

PROSTHETIC MANIPULATOR AND METHOD THEREFOR

FIELD

Aspects of various embodiments are directed to manipulation of prosthetics.

BACKGROUND

Prostheses can be useful to enhance the life experience of users, such as for those who lose or are born without a portion of a limb. As the operability of such prostheses improves, so does the experience of the user. Accordingly, prosthetics have continued to develop over the years to provide enhanced capabilities.

As features are added to prostheses, their complexity also tends to increase. For instance, where mechanical control and actuation are implemented, related componentry can tend to be bulky and require significant power. Other issues with prostheses relate to the challenges that users face in using them. For instance, balance is a major challenge for persons with lower limb amputation, with about 52% experiencing a fall annually and with fear of falls being a significant factor in limiting activity. Walking in settings with lateral balance perturbations, such as on uneven terrain or across side-slopes, can be especially problematic. Many lower-limb prostheses have limited motion in ankle inversion/eversion (IE), and even those with significant IE range of motion support this motion through substantial ankle stiffness. Thus perturbations under the foot create an ankle moment, which can in turn perturb lateral balance. Because gait is naturally less stable in the lateral direction, these perturbations have increased impact on the lateral balance ability of persons with lower limb amputation.

These and other matters have presented challenges to the use of prostheses, for a variety of applications

SUMMARY

Various example embodiments are directed to prosthetics components and their implementation, such as prosthetics components for lower limbs.

According to an example embodiment, an apparatus includes first and second manipulators that respectively operate to manipulate a prosthetic foot about first and second axes. A sensor circuit senses movement characteristics relating to the prosthetic foot (e.g., movement of the manipulators, movement of the foot in space, load applied due to movement). The manipulators operate with the sensor circuit to manipulate the prosthetic foot about the first and second axes, in response to the sensed movement characteristics indicating that the prosthetic foot is elevated over a surface.

Another embodiment is directed to a method or methods as follows. A sensor circuit is used to sense movement characteristics of a prosthetic foot, and the prosthetic foot is manipulated about respective axes in response to the sensed movement characteristics indicating that the prosthetic foot is elevated over a surface. Specifically, a first manipulator is used to manipulate the prosthetic foot about a first axis, and a second manipulator is used to manipulate the prosthetic foot about a second axis that is different than the first axis. This approach may involve, for example, training a wearer of the prosthetic foot to balance by applying perturbations to the prosthetic foot that present an imbalance condition.

The above discussion/summary is not intended to describe each embodiment or every implementation of the present disclosure. The figures and detailed description that follow also exemplify various embodiments.

DESCRIPTION OF THE FIGURES

Various example embodiments may be more completely understood in consideration of the following detailed description in connection with the accompanying drawings, in which.

Figure 1A:
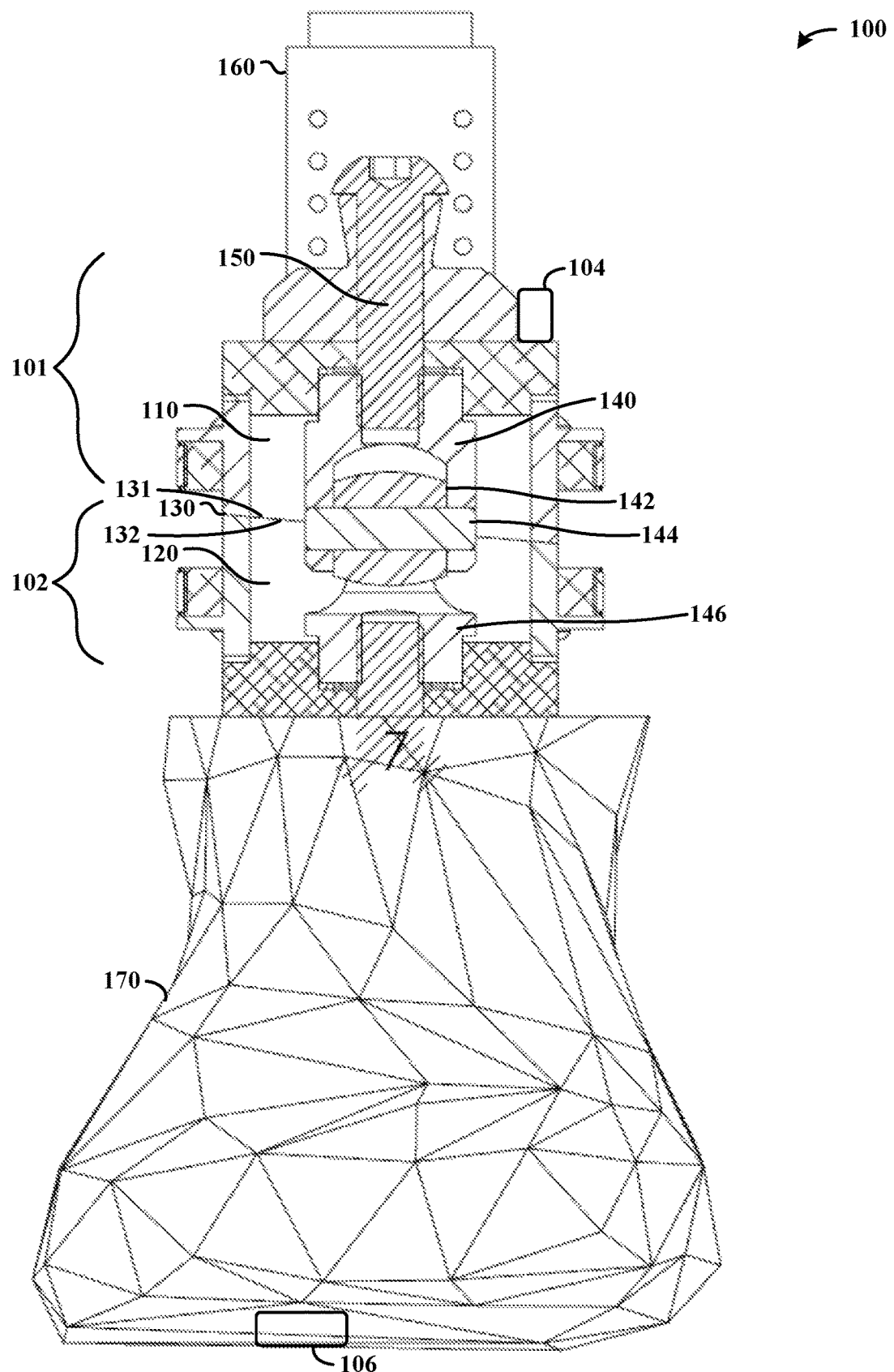
FIG. 1A shows a front view of a prosthetic apparatus in accordance with the present invention.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving prostheses, such as those involving the control of ankle and/or foot-related prostheses. In certain implementations, aspects of the present disclosure have been shown to be beneficial when used in the context of the positioning of a prosthetic foot, such as by doing so via movement while the prosthetic foot is not under load. Various such approaches address challenges as noted herein, such as those relating to bulky and/or relatively high-power actuators. In this context (and as may relate to one or more embodiments) it has been recognized/discovered that a prosthetic foot can be manipulated while it is not loaded, which can allow use of lower-power and/or smaller actuators. This approach can be utilized, for example, to position the prosthetic foot for walking, or to position the prosthetic foot for balance training (e.g., in a controlled setting). While not necessarily so limited, various aspects may be appreciated through a discussion of examples using such exemplary contexts.

According to various example embodiments, aspects of the present disclosure are directed to an apparatus and/or implementation thereof, involving respective manipulators that interact to position a prosthetic foot. Each manipulator operates relative to the other and, together provide the positioning. In this context, the term manipulator refers to a mechanical component that, when moved relative to another such manipulator, provides positioning. In various embodiments, the manipulator includes a drive or other component that generates movement using power, such as provided by a battery. In other embodiments, the manipulator is responsive to a mechanical drive input (e.g., a separate battery/drive component).

As may be implemented in accordance with one or more embodiments, an apparatus includes first and second manipulators that respectively operate to manipulate a prosthetic foot about first and second axes. A sensor circuit senses movement characteristics of the prosthetic foot (e.g., movement, load applied due to movement). The manipulators operate with the sensor circuit to manipulate the prosthetic foot about the first and second axes, in response to the sensed movement characteristics indicating that the prosthetic foot is elevated over a surface. This approach can be implemented, for example, to provide movement of the prosthetic foot while the prosthetic foot is under relatively low/no load, facilitating use of relatively small and/or low-power components for effecting manipulation (e.g., relative to manipulating a prosthetic foot under the load of a user's weight). This approach can further be implemented in a training session to position the prosthetic foot for imbalance training, or in a walking situation in which the foot is positioned when elevated during a stride, relative to a surface upon which the foot will engage.

The manipulators may be implemented in a variety of manners. In some embodiments, the manipulators lock the prosthetic foot in place after manipulating the prosthetic foot about the axes and while the sensed movement characteristics indicate that the prosthetic foot is elevated over the surface. The prosthetic foot may be maintained locked in place while the prosthetic foot is in contact with the surface and under load. For instance, surfaces of the respective manipulators may lock in response to pressure corresponding to a user bearing weight upon the prosthetic foot as it is engaged with the ground. In response to the sensed movement characteristics indicating that the prosthetic foot has been lifted from the surface and is not under load, the manipulators unlock and further manipulate the prosthetic foot about the first and second axes (e.g., for positioning as above). In this context, the manipulators can operate to respectively position, lock and re-position a prosthetic foot during the course of a user's stride. This can be implemented in a training setting to generate perturbations that challenge the user to improve balance, or in a walking setting (or jogging/running) in which the prosthetic foot is positioned to enhance the user's body control.

In various embodiments, each manipulator has surfaces that are maintained in an interface position while the manipulators are moved (e.g., rotated) to impart positioning relative to an incline of the surfaces. For instance, where each manipulator rotates independently from one another, each surface can be implemented with an inclined plane with one manipulator rotating along an axis fixed relative to a patient's leg, and the other manipulator rotating along an axis fixed relative to a foot component. The manipulators can thus be operated with the foot component, such that the axis fixed relative to the foot component is oriented vertically relative to ground when the foot component is used in a standing pose and flat on the ground. In various such embodiments, the respective surfaces can create a moment tending to rotate each of the surfaces along its respective axis due to contact force, and to hold the surfaces in place via friction between the surfaces.

Various embodiments are directed to enhancing the ability of a user to move, such as during walking or running. In some embodiments, the sensor circuit noted above predicts future movement of the prosthetic foot relative to an underlying surface based on the sensed movement characteristics detected over time. The prosthetic foot can then be manipulated about the respective axes based on the predicted future movement of the prosthetic foot.

Sensor circuits and/or mechanical drive circuits as noted herein can be implemented with a processor or processors that utilize sensed characteristics along with special programming to carry out operations that produce a signal or other output that causes movement of manipulators as characterized herein. Such outputs may, for example, be mechanical outputs that cause movement of the manipulators, or an electrical output that is used to control movement within the manipulators. In this context, various embodiments include a motor or motors that drive the manipulators as separate components or integrated within. In some embodiments, a sensor circuit as above includes a processing circuit that predicts future movement of a prosthetic foot by executing an algorithm with the sensed movement characteristics as inputs to the algorithm, and to control movement of the prosthetic foot by generating and outputting a respective control signal for each of the respective manipulators. The manipulators are responsive to the respective control signals by respectively manipulating the prosthetic foot about the first and second axes. For instance, where adaptation relative to an inclined surface is desired, an inclined posture can be applied to a prosthetic foot by adjusting manipulators that operate to effect angular positioning of the foot relative to an ankle connected to the lower leg.

Power for embodiments herein can be provided by a battery circuit. Such a circuit can be implemented within a manipulator, drive component and/or sensor. As noted herein, the power used in this context can be held relatively low by manipulating the prosthetic foot in conditions in which the foot is not under a load.

For instance, a sensor may be implemented to sense ankle moment relative to the prosthetic foot 170 in FIG. 1A, and the manipulators operate with the sensor circuit to manipulate the prosthetic foot about the first and second axes in response to load applied to the foot. A sensor may also be implemented to sense load on the foot, with the manipulators operating with the sensor circuit to manipulate the prosthetic foot about the first and second axes in response to the sensed load.

Various embodiments are directed to a lightweight, low-power ankle adaptor that adjusts ankle alignment in both the dorsiflexion (DF)-plantarflexion (PF) and inversion-eversion (IE) directions. The design uses two short, cylindrical spacers placed at the ankle, with their mating ends cut at complementary angles to form two wedge-shaped inclined planes (upper and lower). These inclined planes rotate independently along axes of (or relative to) the tibia and the foot (e.g., a pylon or other foot component), respectively. If the two planes are aligned in complementary positions, ankle alignment is neutral. If one plane is rotated relative to the other, the mating faces push against each other and force a change in ankle alignment. Using all combinations of upper and lower rotation angles, ankle angles up to twice the face angle of the wedge can be set, in arbitrary directions including DF-PF, IE, or combinations of the two. The inclined surface between the two plates creates a twist-out moment on each plate due to the contact force resulting from the ankle moment, which is held in balance by friction on both the angled face and the opposite flat face. In this context, the moment may tend to rotate each surface along its respective axis.

In connection with one or more embodiments, manipulators as noted herein are adjusted during the swing phase of a step, when body weight forces are not applied (e.g., only the weight and inertia of the foot and shoe create an ankle moment). For instance, in the above embodiment the ankle angle can be set by rotating the inclined plates when body weight forces are not applied. Using this approach, movement of the manipulators can be carried out efficiently. For instance, the actuation moment required to move the inclined plates against weight and friction is easily achievable by small gear motors (e.g., weighing around 25 grams). In various implementations, such an apparatus can accomplish two-axis ankle alignment control while adding relatively little weight (e.g., about 100 grams) to the prosthesis. Two-axis control of prosthesis angle can be implemented to provide adjustments similar to what a natural ankle makes (and which passive prostheses may emulate poorly), such as those involving uphill/downhill stance and locomotion, and side-hill stance and locomotion.

Various embodiments are directed to implementations of prosthetic foot control in a training environment. Such an approach can be implemented to influence walking habits to widen the base of support (BOS) by taking wider steps when walking in a destabilizing environment. In some embodiments, a prosthetic foot is positioned in such a manner that destabilizes the user in a training environment. The user can then adapt his or her gait, which can be carried out under supervision and/or with instruction, to improve the user's adaptive use of the prosthetic foot in destabilized or naturally destabilizing environments.

Two-axis control may also be implemented to intentionally introduce perturbations for training the user to pay better attention to his/her balance, and reduce the incidence of falls in the long term. For instance, a person with lower limb loss can be trained by applying small angular perturbations under the foot to the subject, so he/she is forced to pay attention to his/her balance state. Alternatively, perturbations can be applied during specific training bouts of walking on level ground.

In addition to training, active walking assistance can be provided by moving the prosthesis to adapt to various conditions. For instance, the prosthesis can be adjusted for walking on uneven ground, on ramps, up or down stairs, on slippery surfaces, in snow or a myriad of other conditions. This adjustment may be made, for example, based on classification of a movement pattern of the foot, gait, or other characteristics of movement. The adjustment may also be made, for example, based on sensed terrain conditions as may be realized, for example, using imaging sensors or other sensors that provide an indication of the terrain upon which the user is walking. In some embodiments, adjustments are made to actively control the IE angle of an ankle according to a body's lateral motion to actively resist perturbations. In some implementations, one or both angles of respective manipulators are controlled by the user through measured muscle activity or through a brain-computer interface and/or an interface with user muscles that is utilized to draw information upon which positioning of the prosthetic foot can be carried out.

Respective manipulators may be locked (e.g., prior to impact/the application of force to a foot prosthesis) using one or more of a variety of approaches. For instance, a friction interface between respective planes interfacing between manipulators can be utilized to provide locking. Locking can also be achieved by applying a brake or other force actuator, electronically, magnetically or via other approaches to suit particular applications. In some instances, the locking utilizes force applied by body weight when a foot prosthesis is engaged with a surface and under the body weight.

Figure 1B:
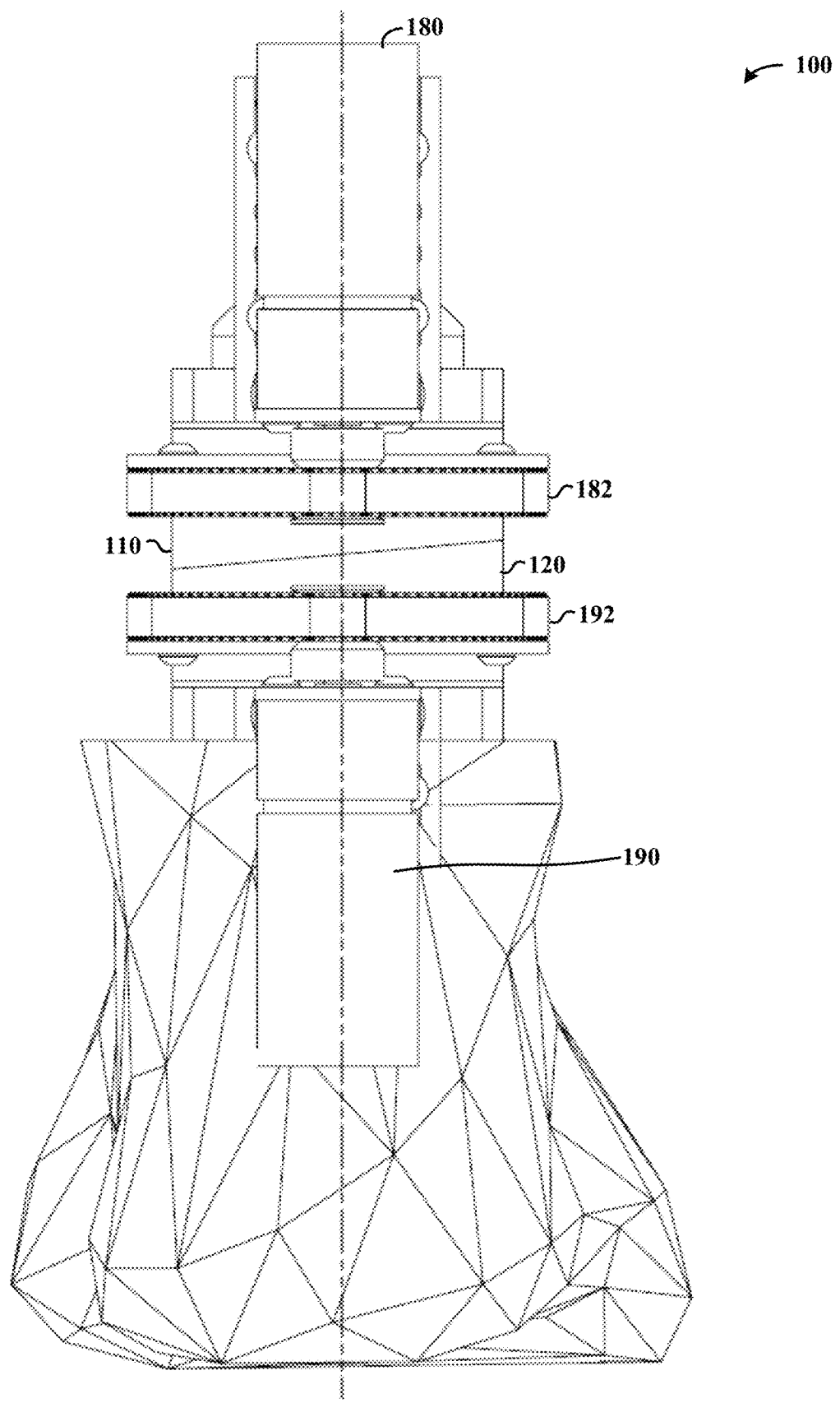
FIG. 1B shows a back view of a prosthetic apparatus in accordance with the present invention.

Turning now to the Figures, FIGS. 1A and 1B show front and back views of a prosthetic apparatus 100 in accordance with the present invention. Referring to FIG. 1A, upper and lower manipulators 101 and 102 respectively have an upper angle-cut cylinder 110 and a lower angle-cut cylinder 120 that interface at 130 along respective surfaces 131 and 132, which may respectively be implemented as inclined planes and rotate about a fixed axis (e.g., the centerline shown in FIG. 1B). A universal-type joint works to maintain the surfaces in contact and restrain the foot from twisting about the leg axis, and includes an upper block 140, spider/coupler 142, central pin 144 and lower block 146. These components are shown by way of example, and can be implemented using a variety of different types of joints/coupling.

The prosthetic apparatus 100 may further include componentry 160 that couples to a user's leg, and/or a prosthetic foot 170. A fastener 150 such as a bolt can be used to couple to componentry 160, which can be fixed relative to a user's leg. A variety of fasteners, prosthetics, and other componentry can be implemented to suit particular embodiments.

FIG. 1B shows the cylinders 110 and 120 from a back view relative to prosthetic foot 170. By way of example, external mechanical drive components 180 and 190 (e.g., motors) are also shown coupled to rotate each cylinder via drive belts 182 and 192. Such an approach may be implemented, for instance, in a training or laboratory setting. Other drive components may be implemented with the apparatus 100, such as via direct-drive motors integrated within and/or coupled to the cylinders, other indirect-drive components, screw drives, and others.

Various other componentry can be implemented with prosthetic apparatuses as characterized herein. Referring again to FIGS. 1A and 1B by way of example, sensors can be implemented to sense force, load, position, acceleration, movement and other characteristics. These sensors can be coupled to (or integrated with) control circuitry that operates to drive respective manipulators for positioning the prosthetic foot. By way of example, a sensor 104 can be implemented to sense motion, images (e.g., ground profile), elevation, angle relative to ground and/or other conditions. These sensed conditions can be used to manipulate the cylinders 110 and 120 (e.g., by passing signals to a controller circuit and/or motor that drives the cylinders to rotate). In this context, a controller circuit can be implemented within the manipulators, or with external mechanical drive components such as shown in FIG. 1B. Similarly, a sensor 106 may be implemented to sense force in the position as shown (in the bottom of prosthetic foot 170) or in another area of the apparatus that is subjected to force when a user of the prosthetic foot 170 is applying body weight thereto. The sensor 106 may also be implemented to sense characteristics noted above as being implemented with sensor 104.

Figure 2:
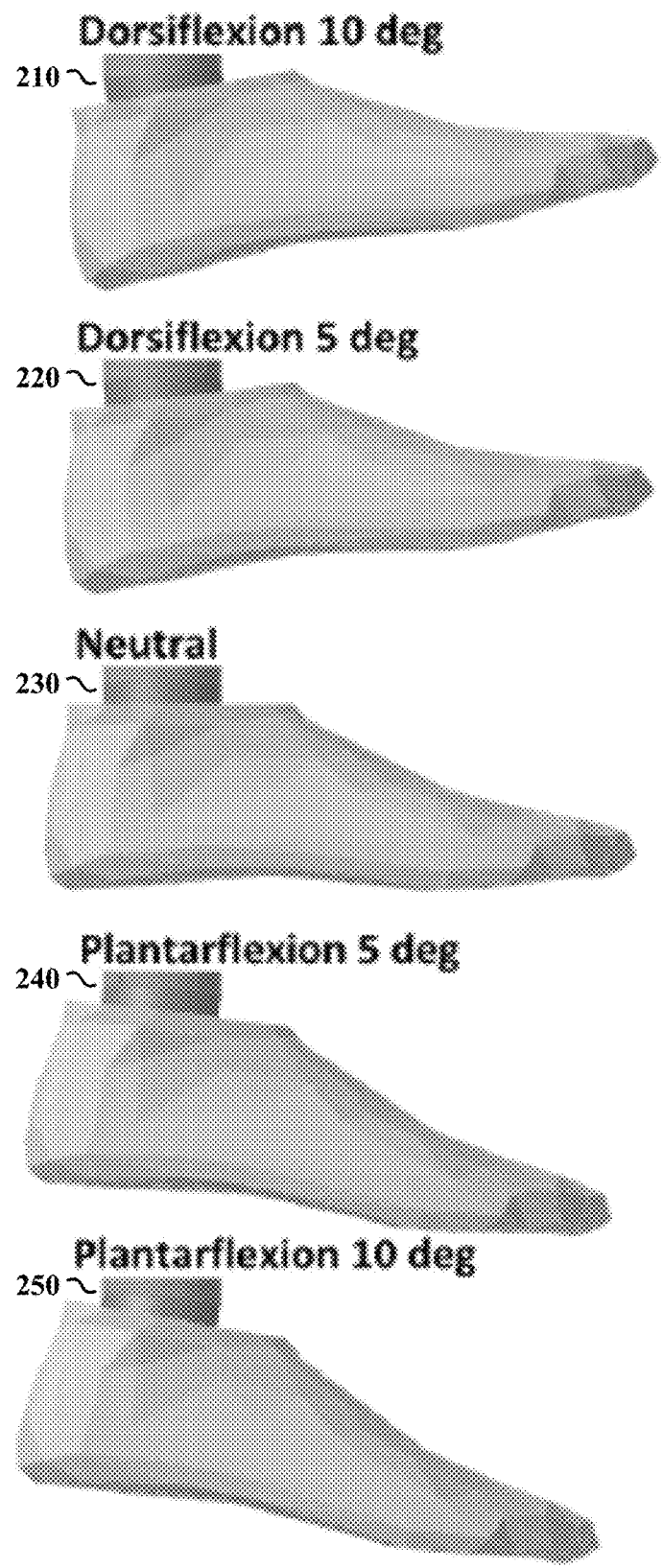
FIG. 2 shows a prosthetic apparatus at various positions, in accordance with one or more embodiments.
Figure 3:
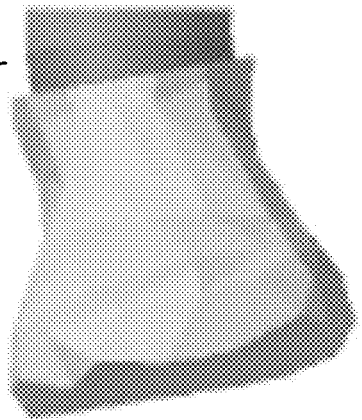
FIG. 3 shows a prosthetic apparatus at various positions, in accordance with one or more embodiments.
Figure 3:
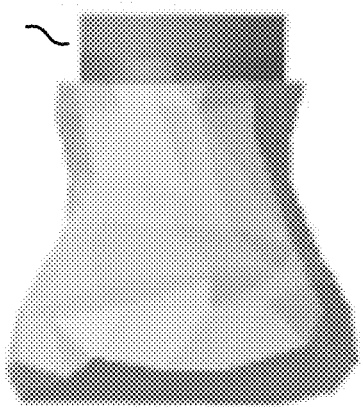
Figure 3:
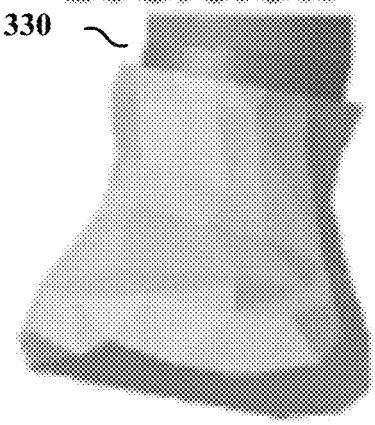

FIGS. 2 and 3 show prosthetic apparatuses at various positions, in accordance with one or more embodiments. The embodiments shown may, for example, be implemented with respective manipulators as shown in FIG. 1. Beginning with FIG. 2, respective interfacing manipulators are shown at 210 and 220 respectively positioned to provide 10 degrees and 5 degrees of dorsiflexion for a prosthetic foot. The manipulators are shown at 230 to provide a neutral position, and at 240 and 250 to respectively provide 5 and 10 degrees of plantarflexion. In FIG. 3, the manipulators are shown at an inversion position (310), neutral position (320), and eversion position (330).

Figure 4:
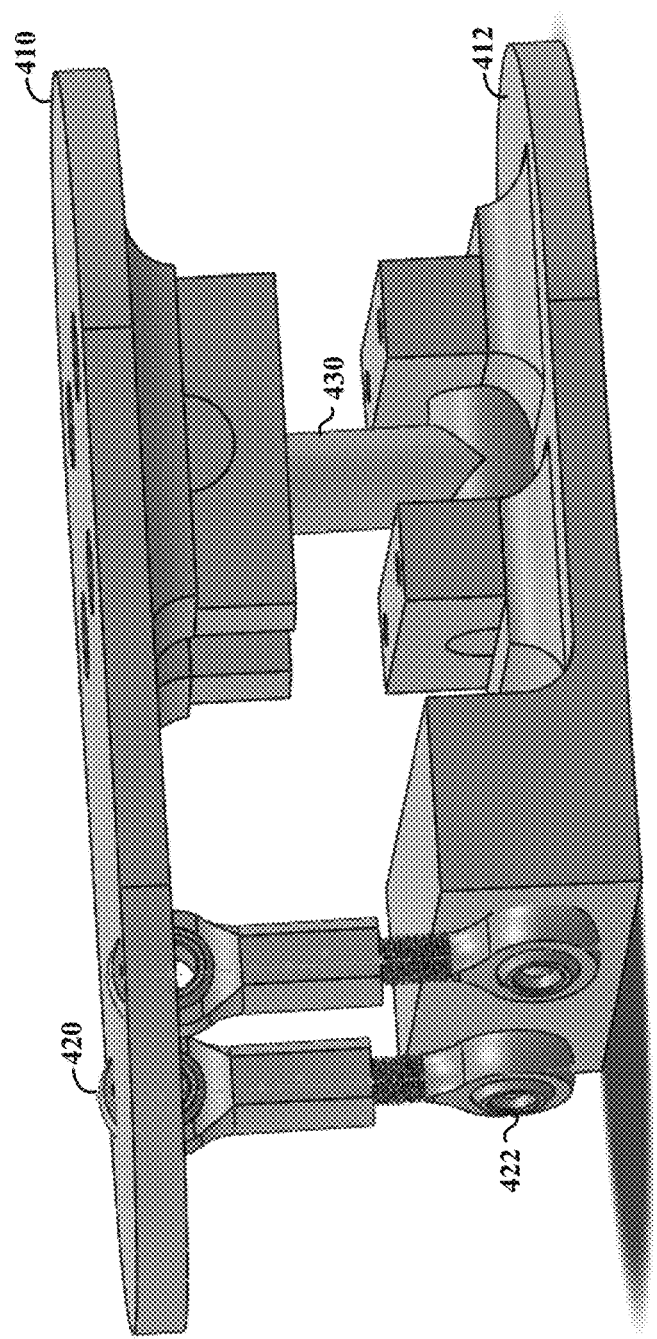
FIG. 4 shows a prosthetic apparatus, in accordance with another embodiment.

FIG. 4 shows a prosthetic apparatus 400, in accordance with one or more embodiments. The apparatus 400 includes two platforms 410 and 412, which can respectively be coupled to a prosthetic foot and a user's leg. By way of example, the platforms are shown coupled with tie rods at 420 and 422 (with an adjacent tie rod not labeled), and another pivoting rod 430. In various implementations, the tie rods are replaced with power screws that spin to actuate the platforms relative to one another.

Various blocks, modules or other circuits may be implemented to carry out one or more of the operations and activities described herein and/or shown in the figures. In these contexts, a "block" (also sometimes "logic circuitry" or "module") is a circuit that carries out one or more of these or related operations/activities (e.g., sensing, generating a control signal for operating an actuator, or positioning a manipulator). For example, in certain of the above-discussed embodiments, one or more modules are discrete logic circuits or programmable logic circuits configured and arranged for implementing these operations/activities, such as with controllers that can be implemented with the apparatus(es) shown the Figures. In certain embodiments, such a programmable circuit is one or more computer circuits programmed to execute a set (or sets) of instructions that control the alignment of a prosthetic foot. The instructions (and/or configuration data) can be in the form of firmware or software stored in and accessible from a memory (circuit). As an example, first and second modules may include a combination of a CPU hardware-based circuit and a set of instructions in the form of firmware, where the first module includes a first CPU hardware circuit with one set of instructions and the second module includes a second CPU hardware circuit with another set of instructions. Such instructions may also be implemented for training a user via the application of perturbations as discussed herein.

Certain embodiments are directed to a computer program product (e.g., nonvolatile memory device), which includes a machine or computer-readable medium having stored thereon instructions which may be executed by a computer (or other electronic device) to perform these operations/activities.

Based upon the above discussion and illustrations, those skilled in the art will readily recognize that various modifications and changes may be made to the various embodiments without strictly following the exemplary embodiments and applications illustrated and described herein. For example, additional manipulators may be used to provide a further degree or degrees of freedom. Different angles of interface and different types of interfaces may be used to achieve prosthetic positioning. Further, other prosthetics may be similarly controlled, such as those pertaining to knee or hip movement. In addition, the various embodiments described herein may be combined in certain embodiments, and various aspects of individual embodiments may be implemented as separate embodiments. The various embodiments described herein may also be combined in certain embodiments, and various aspects of individual embodiments may be implemented as separate embodiments. Such modifications do not depart from the true spirit and scope of various aspects of the invention, including aspects set forth in the claims.

What is claimed is:

1. An apparatus comprising:
    a first manipulator configured and arranged to manipulate a prosthetic foot block about a first axis;
    a second manipulator configured and arranged to manipulate the prosthetic foot block about a second axis that is different than the first axis; and
    a sensor circuit, including processor circuitry, configured and arranged to sense movement characteristics of the prosthetic foot block while a prosthetic foot connected to the prosthetic foot block is elevated over a surface, the first and second manipulators being configured and arranged with the sensor circuit to manipulate the prosthetic foot block about the first and second axes in response to the sensed movement characteristics indicating that the prosthetic foot is elevated over a surface, and to lock the prosthetic foot block in place while the prosthetic foot block is under load corresponding to the prosthetic foot being in contact with the surface.

2. The apparatus of claim 1, wherein the first and second manipulators are configured and arranged with the processor circuitry to lock the prosthetic foot block in place, after the processor circuitry controls the first and second manipulators for manipulating the prosthetic foot block about the first and second axes in response to the sensed movement characteristics indicating that the prosthetic foot block is elevated over the surface.

3. The apparatus of claim 2, wherein the first and second manipulators are configured and arranged with the processor circuitry to maintain the prosthetic foot block locked in place until the prosthetic foot block is not under load corresponding to the prosthetic foot being in contact with the surface.

4. The apparatus of claim 3, wherein the first and second manipulators are configured and arranged with the processor circuitry to unlock and further manipulate the prosthetic foot block about the first and second axes in response to the sensed movement characteristics indicating that the prosthetic foot has been lifted away from the surface and is not under load.

5. The apparatus of claim 1, wherein
    the first manipulator has a first surface; and
    the second manipulator has a second surface interfaced and in direct contact with the first surface and configured and arranged with the first manipulator to position the prosthetic foot block in response to manipulation of the first and second surfaces relative to one other.

6. The apparatus of claim 5, wherein
    the first and second manipulators are configured and arranged to rotate independently from one another;
    the first surface is an inclined plane configured and arranged to rotate along an axis fixed relative to a patient's leg connected to the first manipulator; and
    the second surface is an inclined plane configured and arranged to rotate along an axis fixed relative to a prosthetic foot component connected to the second manipulator via the prosthetic foot block.

7. The apparatus of claim 6, wherein the first and second manipulators are configured and arranged with the prosthetic foot block to orient the axis fixed relative to the prosthetic foot component vertically relative to ground when the prosthetic foot is in a standing pose and flat on the ground.

8. The apparatus of claim 5, wherein the first and second surfaces are configured and arranged with one another to create a moment tending to rotate each of the first and second surfaces along their respective axes due to contact force, and to hold the surfaces in place via friction between the surfaces.

9. The apparatus of claim 1, wherein
the sensor circuit is configured and arranged to predict future movement of the prosthetic foot relative to the surface based on the sensed movement characteristics detected over time, and
the sensor circuit is configured and arranged with the first and second manipulators to manipulate the prosthetic foot block about the first and second axes based on the predicted future movement of the prosthetic foot.

10. The apparatus of claim 9, wherein the sensor circuit includes a processing circuit configured and arranged to predict the future movement of the prosthetic foot by executing an algorithm with the sensed movement characteristics as inputs to the algorithm, and to control movement of the prosthetic foot block by generating and outputting a respective control signal for each of the respective first and second manipulators, the first and second manipulators being responsive to the respective control signals by respectively manipulating the prosthetic foot block about the first and second axes.

11. The apparatus of claim 1, wherein
movement of the first manipulator is limited to a single degree of freedom via rotation about the first axis;
movement of the second manipulator is limited to a single degree of freedom via rotation about the second axis; and
the first and second manipulators are configured and arranged to manipulate the prosthetic foot block about the first and second axes in response to mechanical inputs provided to each of the manipulators.

12. The apparatus of claim 11, further including a battery circuit configured and arranged to provide power to the first and second manipulators, the first and second manipulators being configured and arranged to manipulate the prosthetic foot using the power provided by the battery circuit.

13. The apparatus of claim 1, further including:
a first motor configured and arranged to manipulate the first manipulator; and
a second motor configured and arranged to manipulate the second manipulator.

14. The apparatus of claim 13, wherein:
the first manipulator includes the first motor; and
the second manipulator includes the second motor.

15. The apparatus of claim 1, wherein the sensor circuit is configured and arranged to sense ankle moment relative to the prosthetic foot block, and the first and second manipulators are configured and arranged with the sensor circuit to manipulate the prosthetic foot block about the first and second axes in response to load applied to the prosthetic foot.

16. The apparatus of claim 1, wherein the sensor circuit is configured and arranged to sense load on the prosthetic foot block, and the first and second manipulators are configured and arranged with the sensor circuit to manipulate the prosthetic foot block about the first and second axes in response to the sensed load.

17. The apparatus of claim 1, further including the prosthetic foot.

18. The apparatus of claim 1, wherein the first and second manipulator are configured and arranged to manipulate the prosthetic foot block by providing dorsiflexion (DF)-plantarflexion (PF) and inversion/eversion (IE) movement.

19. A method comprising:
utilizing a sensor circuit including processor circuitry, sensing movement characteristics of a prosthetic foot block while the prosthetic foot block and a prosthetic foot connected to the prosthetic foot block is elevated over a surface;
manipulating the prosthetic foot block about first and second axes in response to the sensed movement characteristics indicating that the prosthetic foot is elevated over the surface, by
using a first manipulator to manipulate the prosthetic foot block about the first axis,
using a second manipulator to manipulate the prosthetic foot block about a second axis that is different than the first axis; and
locking the prosthetic foot block in place in response to sensing that the prosthetic foot block is under load corresponding to the prosthetic foot being in contact with a surface.

20. The method of claim 19, further including using the first and second manipulators to apply perturbations to the prosthetic foot block that present an imbalance condition.

21. The method of claim 19, wherein manipulating the prosthetic foot block about the first and second axes includes providing active assistance to a wearer of the prosthetic foot by positioning the prosthetic foot block based on conditions of an environment in which the wearer is moving.

22. The method of claim 21, wherein providing active assistance includes adjusting the prosthetic foot block based on movement sensed via the sensing circuit.

23. The method of claim 19, wherein manipulating the prosthetic foot block about the first and second axes includes controlling at least one of the first and second manipulators using an interface between a wearer of the prosthetic foot and the first and second manipulators.

24. The method of claim 19, further including locking the first and second manipulators in place after manipulating the prosthetic foot block about the first and second axes and prior to detecting the prosthetic foot striking a surface.

\* \* \* \* \*